United States Patent
Kamen et al.

(10) Patent No.: US 11,980,776 B2
(45) Date of Patent: May 14, 2024

(54) RADIATION-INDUCED TOXICITY AND MACHINE LEARNING

(71) Applicant: SIEMENS HEALTHINEERS AG, Forchheim (DE)

(72) Inventors: Ali Kamen, Skillman, NJ (US); Bin Lou, Princeton, NJ (US); Fernando Vega, Erlangen (DE)

(73) Assignee: Siemens Healthineers AG, Forchheim (DE)

( * ) Notice: Subject to any disclaimer, the term of this patent is extended or adjusted under 35 U.S.C. 154(b) by 361 days.

(21) Appl. No.: 17/649,824

(22) Filed: Feb. 3, 2022

(65) Prior Publication Data
US 2022/0257978 A1    Aug. 18, 2022

(51) Int. Cl.
| | |
|---|---|
| *A61N 5/10* | (2006.01) |
| *G06T 7/00* | (2017.01) |
| *G16H 20/40* | (2018.01) |
| *G16H 50/30* | (2018.01) |

(52) U.S. Cl.
CPC .......... *A61N 5/1039* (2013.01); *G06T 7/0012* (2013.01); *G16H 20/40* (2018.01); *G16H 50/30* (2018.01); *G06T 2207/20081* (2013.01); *G06T 2207/30096* (2013.01)

(58) Field of Classification Search
CPC .... A61N 5/1039; A61N 5/103; G06T 7/0012; G06T 2207/20081; G06T 2207/30096; G16H 20/40; G16H 50/30; G16H 70/20; G06N 3/045; G06N 3/084; G06N 20/00
See application file for complete search history.

(56) References Cited

U.S. PATENT DOCUMENTS

2017/0083682 A1 * 3/2017 McNutt ............... A61N 5/1031
2019/0371450 A1    12/2019 Lou et al.

FOREIGN PATENT DOCUMENTS

CN       109671499 A      4/2019

OTHER PUBLICATIONS

B Georgescu, et. al., Machine Learning Automatically Detects COVID-19 using Chest CTs in a Large Multicenter Cohort, https://arxiv.org/abs/2006.04998. pp. 1-27.
Lou, Bin, et al. "An image-based deep learning framework for individualising radiotherapy dose: a retrospective analysis of outcome prediction." The Lancet Digital Health 1.3 (2019): e136-e147.
European Search Report for European Application No. 21157289.6-112 mailed Aug. 9, 2021.
(Continued)

*Primary Examiner* — Courtney D Thomas (57) ABSTRACT

Risks of radiation-induced toxicity associated with a radiotherapy treatment of a target region of a patient are predicted. Data associated with a region of interest comprising the target region is received. The received data includes a predefined dose map of the radiotherapy treatment and pre-radiotherapy-treatment imaging data of the region of interest. A trained machine-learning algorithm is applied to the received data. The trained machine-learning algorithm generates at least one toxicity indicator based on the received data. The at least one toxicity indicator is indicative of the risks of the radiation-induced toxicity.

17 Claims, 4 Drawing Sheets

(56) References Cited

OTHER PUBLICATIONS

H. Aerts et al., "Decoding tumour phenotype by noninvasive imaging using a quantitative radiomics approach," NatureCommunications, 2014. pp. 1-8.

Kong FM, Wang S. Nondosimetric risk factors for radiation-induced lung toxicity. Semin Radiat Oncol. 2015;25 (2):100-109.doi:10.1016/j.semradonc.2014.12.003.

Men, Kuo, et al. "A deep learning model for predicting xerostomia due to radiation therapy for head and neck squamous cell carcinoma in the RTOG 0522 clinical trial." International Journal of Radiation Oncology* Biology* Physics 105.2 (2019): 440-447.

R Gillies et al., "Radiomics: images are more than pictures, they are data," Radiology, 2015. pp. 563-577.

Xin, Zhen et al: "Deep convolutional neutral network with transfer learning for rectum toxicity prediction in cervical cancer radiotherapy: a feasibility study"; Physics in Medicine and Biology, Institute of Physics Publishing, Bristol GB, vol. 62, No. 21, Oct. 11, 2017.

\* cited by examiner

RADIATION-INDUCED TOXICITY AND MACHINE LEARNING

RELATED APPLICATION

This application claims the benefit of 21157289.6, filed Feb. 16, 2021, which is hereby incorporated by reference in its entirety.

TECHNICAL FIELD

Various embodiments of the disclosure relate to methods and devices for predicting radiation-induced toxicity associated with a radiotherapy treatment by utilizing a machine-learning algorithm.

BACKGROUND

Radiotherapy uses charged particles, e.g., electrons or ions, to treat cancer. It is also possible to use photons. The particles deposit energy at a tumor to physically destroy the tumor.

Radiotherapy has been a useful treatment for many types of cancer. Nonetheless, it has been observed that some patients subsequently experience radiation-induced toxicity. This is explained in further detail hereinafter.

One example employs radiotherapy to treat non-small cell lung cancer (NSCLC). Stereotactic body radiation therapy (SBRT) is the standard of care for medically inoperable patients with early-stage NSCLC. However, the lung is a radiosensitive organ and radiation pneumonitis—as an example of radiation-induced toxicity—can occur after exposure to radiation of larger than 5 Gray in only a few months. Lung pneumonitis is manifested by loss of epithelial cells, edema, inflammation, fibrosis, and occlusion of airways, blood vessels, and sacs. The vulnerability of patients to be subject to radiation pneumonitis is directly correlated with any underlying preexisting disease of the lungs. Additionally, standard approaches, such as SBRT, for radiotherapy that demonstrate efficacy for a population may not achieve optimal results for individual patients.

Consequently, it is difficult to individualize current standard radiotherapy treatments, such as SBRT for treating NSCLC, based on anatomical and physiological characteristics of individual patients; therefore, it is difficult to select a radiotherapy treatment that is most likely to be adapted to an individual patient to maximize the likelihood of treatment response while minimizing the risk of adverse effects, such as radiation-induced toxicity.

SUMMARY

Therefore, there is a need for advanced techniques of planning a radiotherapy treatment. In particular, there is a need for advanced techniques of predicting—prior to a radiotherapy treatment—a patient's vulnerability to radiation-induced toxicity.

This need is met by the features of the embodiments.

A method for predicting risks of radiation-induced toxicity associated with a radiotherapy treatment of a target region of a patient is disclosed. The method includes receiving data associated with a region of interest including the target region. The received data includes a predefined dose map of the radiotherapy treatment and pre-radiotherapy-treatment imaging data of the region of interest. The method further includes applying a trained machine-learning algorithm to the received data, and generating, by the trained machine-learning algorithm, at least one toxicity indicator based on the received data. The at least one toxicity indicator is indicative of the risks of the radiation-induced toxicity.

A method of performing a training of a machine-learning algorithm for predicting risks of radiation-induced toxicity associated with a radiotherapy treatment of a target region of a patient is disclosed. The method includes receiving multiple instances of training data associated with a region of interest including the target region and multiple instances of reference data. Each one of the multiple instances of the reference data corresponds to a respective instance of the training data. Each one of the multiple instances of the training data includes a dose map of the radiotherapy treatment and pre-radiotherapy-treatment imaging data of the region of interest. Each instance of the multiple instances of the reference data includes at least one diagnosed toxicity indicator indicative of diagnosed risks of radiation-induced toxicity. The method further includes processing the multiple instances of the training data by the machine-learning algorithm, and generating, by the machine-learning algorithm and for each one of the multiple instances of the training data, at least one respective estimated toxicity indicator indicative of estimated risks of radiation-induced toxicity. The method further includes performing the training of the machine-learning algorithm by updating parameter values of the machine-learning algorithm based on a comparison between the diagnosed toxicity indicators and corresponding estimated toxicity indicators.

A device includes a processing unit (processor), a memory unit (memory) and an input/output interface. The processing unit is configured to execute a program stored in the memory unit to perform a method for predicting risks of radiation-induced toxicity associated with a radiotherapy treatment of a target region of a patient. The method includes receiving data associated with a region of interest including the target region. The received data includes a predefined dose map of the radiotherapy treatment and pre-radiotherapy-treatment imaging data of the region of interest. The method further includes applying a trained machine-learning algorithm to the received data, and generating, by the trained machine-learning algorithm, at least one toxicity indicator based on the received data. The at least one toxicity indicator is indicative of the risks of the radiation-induced toxicity.

A device includes a processing unit, a memory unit and an input/output interface. The processing unit is configured to execute a program stored in the memory unit to perform a method of performing a training of a machine-learning algorithm for predicting risks of radiation-induced toxicity associated with a radiotherapy treatment of a target region of a patient. The method includes receiving multiple instances of training data associated with a region of interest including the target region and multiple instances of reference data. Each one of the multiple instances of the reference data corresponds to a respective instance of the training data. Each one of the multiple instances of the training data includes a dose map of the radiotherapy treatment and pre-radiotherapy-treatment imaging data of the region of interest. Each instance of the multiple instances of the reference data includes at least one diagnosed toxicity indicator indicative of diagnosed risks of radiation-induced toxicity. The method further includes processing the multiple instances of the training data by the machine-learning algorithm, and generating, by the machine-learning algorithm and for each one of the multiple instances of the training data, at least one respective estimated toxicity indicator indicative of estimated risks of radiation-induced toxicity. The method additionally includes performing the training of the machine-learning algorithm by updating parameter values of the machine-learning algorithm based on a comparison between the diagnosed toxicity indicators and corresponding estimated toxicity indicators.

A computer program product or a computer program or a non-transitory computer-readable storage medium includes program code (instructions). The program code can be executed by at least one processor. Executing the program code causes the at least one processor to perform a method for predicting risks of radiation-induced toxicity associated with a radiotherapy treatment of a target region of a patient. The method includes receiving data associated with a region of interest including the target region. The received data includes a predefined dose map of the radiotherapy treatment and pre-radiotherapy-treatment imaging data of the region of interest. The method further includes applying a trained machine-learning algorithm to the received data, and generating, by the trained machine-learning algorithm, at least one toxicity indicator based on the received data. The at least one toxicity indicator is indicative of the risks of the radiation-induced toxicity.

A computer program product or a computer program or a non-transitory computer-readable storage medium includes program code. The program code can be executed by at least one processor. Executing the program code causes the at least one processor to perform a method of performing a training of a machine-learning algorithm for predicting risks of radiation-induced toxicity associated with a radiotherapy treatment of a target region of a patient. The method includes receiving multiple instances of training data associated with a region of interest including the target region and multiple instances of reference data. Each one of the multiple instances of the reference data corresponds to a respective instance of the training data. Each one of the multiple instances of the training data includes a dose map of the radiotherapy treatment and pre-radiotherapy-treatment imaging data of the region of interest. Each instance of the multiple instances of the reference data includes at least one diagnosed toxicity indicator indicative of diagnosed risks of radiation-induced toxicity. The method further includes processing the multiple instances of the training data by the machine-learning algorithm, and generating, by the machine-learning algorithm and for each one of the multiple instances of the training data, at least one respective estimated toxicity indicator indicative of estimated risks of radiation-induced toxicity. The method additionally includes performing the training of the machine-learning algorithm by updating parameter values of the machine-learning algorithm based on a comparison between the diagnosed toxicity indicators and corresponding estimated toxicity indicators.

It is to be understood that the features mentioned above and those yet to be explained below may be used not only in the respective combinations indicated, but also in other combinations or in isolation without departing from the scope of the invention.

DETAILED DESCRIPTION OF EMBODIMENTS

In the following, embodiments of the invention will be described in detail with reference to the accompanying drawings. It is to be understood that the following description of embodiments is not to be taken in a limiting sense. The scope of the invention is not intended to be limited by the embodiments described hereinafter or by the drawings, which are taken to be illustrative only.

The drawings are to be regarded as being schematic representations and elements illustrated in the drawings, which are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various examples described herein generally relate to techniques of planning a radiotherapy treatment. The radiotherapy treatment can rely on irradiating a tumor to destroy cancer cells. It is possible to use charged particles such as ions or electrons, or even high-energy photons.

Thus, in other words, radiotherapy (also called radiation therapy) is a cancer treatment that uses high doses of radiation to kill cancer cells and shrink tumors. At high doses, radiation therapy kills cancer cells or slows their growth by damaging their deoxyribonucleic acid (DNA). Cancer cells whose DNA is damaged beyond repair stop dividing or die. When the damaged cells die, they are broken down and removed by the body. Radiation therapy does not necessarily kill cancer cells right away. It takes days or weeks of treatment before DNA is damaged enough for cancer cells to die. Then, cancer cells keep dying for weeks or months after radiation therapy ends.

As a general rule, there are two main types of radiation therapy, external beam radiation therapy and internal radiation therapy. External beam radiation therapy is generated by a machine that aims the radiation at a target region. The incident path of the radiation is adjustable by relatively positioning the machine with respect to the patient. On the other hand, internal radiation therapy is a treatment in which a source of radiation is put inside the patient's body. The radiation source can be solid or liquid, which are called brachytherapy and systemic therapy, respectively.

Various techniques described herein generally relate to predicting risks of radiation-induced toxicity associated with the radiotherapy treatment. More specifically, at least one toxicity indicator indicative of the risks of the radiation-induced toxicity can be determined. Thereby, a prediction of a risk of adverse side-effects of the radiotherapy treatment can be made.

Various options are generally available for implementing the at least one toxicity indicator. Some examples are summarized in TAB. 1 below.

TABLE 1

Various options for a least one toxicity indicator that is generated by the techniques described herein, to predict the risks of radiation-induced toxicity. According to various examples described herein, it is possible to obtain multiple such toxicity indicators or only one toxicity indicator.

| | Brief description | Detailed examples |
|---|---|---|
| I | Aggregated risk score | The aggregated risk score can provide an overall risk of the patient suffering from radiation-induced toxicity after the radiotherapy treatment. The aggregated risk score can be of low dimensionality, e.g., not including a spatial resolution. The aggregated risk score can be defined with respect to a predefined metric. Example metrics may include thresholds or non-linear activations resulting in a significant aggregated risk score once a certain threshold - e.g., with respect to a total accumulated dose, etc. - have been crossed. The aggregated risk score may be obtained based on a manifestation of the toxicity and its severity, e.g., a score on scales 1 to 5, 1 noting mild, and 5 noting severe. |
| II | Dose sensitivity | A dose sensitivity can characterize effects of doses defined by the predefined dose map on the radiation-induced toxicity. In other words, a dose sensitivity can specify a change of the radiation-induced toxicity triggered by a change of the doses defined by the dose map. There are various options available for specifying such input-output dependencies, e.g., it would be possible to use a nomogram. |
| III | Toxicity area map | A toxicity area map can include a spatial resolution within a region of interest. Here, local hotspots can be identified where the surrounding tissue adjacent to the tumor is exposed to radiation-induced toxicity. The toxicity area map of the region of interest 2020 indicates where within the region of interest 2020 tissues suffer from radiation-induced toxicity. The large the toxicity area, the serious the radiation-induced toxicity. |

It would be possible to use the at least one toxicity indicator to adjust a treatment plan of the radiotherapy treatment. Various options are available for adjusting the treatment plan. A dose map (cf. TAB. 2, example I) could be adjusted. For example, it would be possible to decrease a dose that is administered by the radiotherapy treatment. It would be possible to adjust an energy of the particles. It would be possible to change and impact path of the particles. Such tasks could be computer-implemented using a respective algorithm.

According to various examples, it is possible to determine the at least one toxicity indicator by applying a trained machine-learning algorithm, such as a deep neural network, to input data.

According to the various examples described herein, various options are available for implementing the input data. Some examples are listed in TAB. 1.

TABLE 2

Various options for input data to be considered when determining at least one toxicity indicator, cf. TAB. 1. According to the various examples described herein, such another input data can be combined with each other and provided as aggregated inputs to a machine-learning algorithm, to then generate at least one toxicity indicator. For example, different channels of an input vector can be associated with different types of input data according to the examples described herein. Various techniques are based on the finding that such input data is listed in TAB. 2 can show strong correlations with the risk of radiation-induced toxicity and, therefore, are suitable to be used as input data for making such a prediction.

| | Brief description | Detailed examples |
|---|---|---|
| I | Dose map | The dose map can specify the spatially-resolved dose deposited by radiation during the radiotherapy treatment. For instance, different types of radiation are characterized by a different spatial activation profiles, e.g., specifying the dose deposited per area depending on a propagation path in the tissue and the energy of the particles. Based on such considerations, it is possible to calculate the dose map. One can readily compute the dose map distribution resulting from radiation beams of photons, electrons, or mixtures of these impinging on a regularly shaped, flat surface, homogeneous unit density phantom. For individual patient it is possible to take into account the irregularly shaped anatomy and different tissue types of varying densities and atomic composition (called heterogeneities). The dose map may be based on at least one of the following dosimetric parameters: a percentage depth dose (PDD), a tissue-air ration (TAR), a tissue-phantom ratio (TPR), or a tissue-maximum ratio (TMR). |
| II | Imaging data | Pre-radiotherapy-treatment imaging data can be used to capture the anatomy of the patient in the target region and around the target region. For instance, organs next to the target region could be identified. Various imaging modalities may be used such as Magnetic resonance Imaging (MRI), computed tomography (CT), ultrasound imaging, positron emission tomography (PET) imaging, to name just a few. The pre-radiotherapy-treatment imaging data may be 1D, 2D, or 3D. In some special scenarios, the pre-radiotherapy-treatment imaging data may also be 4D (i.e., x, y, z, and t), such as 4D MRI images. |
| III | Dose level | The dose level can specify an aggregated dose deposited at and around the target region in the region of interest. |
| IV | Clinical stage of tumor | The clinical stage of the tumor can specify, e.g., how localized the tumor is and whether the tumor has spread and grown. A clinical stage is an estimate of the extent of a cancer based on results of physical exams, imaging tests (x-rays, CT scans, etc.), endoscopy exams, and any biopsies that are done before treatment starts. For some cancers, the results of other tests, such as blood tests, are also used in clinical staging. The clinical stage is often a key part of deciding the best treatment |

TABLE 2-continued

Various options for input data to be considered when determining at least one toxicity indicator, cf. TAB. 1. According to the various examples described herein, such another input data can be combined with each other and provided as aggregated inputs to a machine-learning algorithm, to then generate at least one toxicity indicator. For example, different channels of an input vector can be associated with different types of input data according to the examples described herein. Various techniques are based on the finding that such input data is listed in TAB. 2 can show strong correlations with the risk of radiation-induced toxicity and, therefore, are suitable to be used as input data for making such a prediction.

| | Brief description | Detailed examples |
|---|---|---|
| V | Clinical information re patient | options. The clinical stage can also be used when trying to get an idea of what a person's outlook (prognosis) might be. For example, the survival rates for most types of cancer are based mainly on the stage at the time of diagnosis. Various clinical data such as comorbidities of the patient and/or demographics of the patient - e.g., age, drug prescriptions, use of narcotics, et cetera - can be considered as input data. Comorbidities of a patient having cancer indicate other diseases suffered by the patient, such as hypertension, diabetes, heart diseases and etc. Demographics of the patient may include at least one of an age, a gender, an address, an ethnicity, a blood type, contact information, allergies, major diagnoses, major medical history, and so on. |

Figure 1:
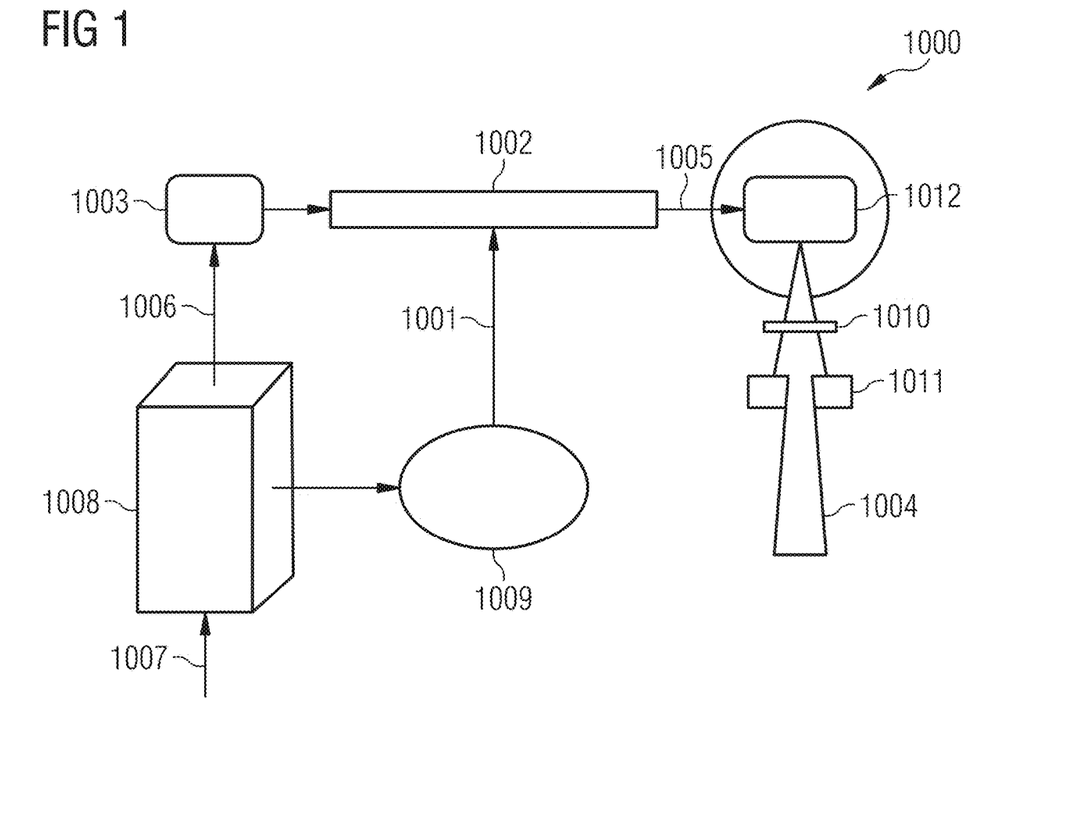
FIG. 1 is a schematic illustration of a high-energy bent-beam medical linear accelerator for a radiotherapy treatment according to various examples.

FIG. 1 schematically illustrates a radiation source for providing radiation for a radiotherapy treatment. This serves as an example of a hardware implementation of a medical tool used for radiation therapy. Today, medical linear accelerators (referred to as linacs) account for most of the operational megavoltage radiotherapy treatment units in clinical use. FIG. 1 is a block diagram of a high-energy bent-beam medical linear accelerator 1000 showing the major components. The linac 1000 uses microwave pulses 1001, e.g., having frequencies in the S-band microwave region (e.g., 2,856 MHz,) to generate an electric field. The microwave radiation of the microwave pulse 1001 is propagated through an accelerator waveguide 1002 and electrons that are generated by an electron gun 1003 and used to create an X-ray—i.e., photon—(or electron) beam for treatment 1004 are injected into the accelerator waveguide 1002 and accelerated by the generated electric field. The structure of the accelerator waveguide 1002 includes a stack of cylindrical metal cavities having an axial hole 1005 through which the accelerated electrons pass. The linac 1000 further includes a modulator 1008 that converts a line AC (analog current) power 1007 to an RF (radio frequency) power source 1009 needed for the production of the microwave pulse 1001, and a high voltage pulse 1006 supplied to the electron gun 1003.

Once accelerated, the accelerated high-energy electrons emerge at the axial hole 1005 and are directed to strike a metal target (not shown in FIG. 1). This abrupt stopping of the electrons results in the conversion of their kinetic energy partially to heat in the metal target and partially to the production of bremsstrahlung X-rays. Because the accelerator waveguide 1002 is typically placed horizontally or at some angle with respect to the horizontal, the electrons are bent by a bending system 1012 and through a suitable angle, usually 90 or 270 degrees between the accelerator waveguide 1002 and the X-ray target. In addition, the linac 1000 also includes a dosimetry system 1010 and/or collimation system 1011 for adjusting radiation doses. The dosimetry system 1010 and/or the collimation system 1011 can be controlled by a computing device, such as a computer or a server (not shown in FIG. 1) directly connected to the linac 1000, a server or a computer remotely connected to the linac 1000 via a network.

The linac 1000 can operate based on a treatment plan that specifies its relative positioning to the patient and the energy of the emitted particles in each position. The duration of the emission can be specified. The treatment plan thus defines a dose map (cf. TAB. 2, example I).

The linac 1000 of FIG. 1 is one example of hardware used for performing a radiation therapy treatment. As a general rule, radiotherapy treatments mentioned in this disclosure may be performed by any one of the following radiotherapy treatment systems: an intensity modulated radiotherapy (IMRT) system, an image-guided radiotherapy (IGRT) system, an intensity modulated art therapy (IMAT) system, a rotational IMRT system, a Tomotherapy IMRT, a CyberKnife® system, a Gamma Knife system, a 4-D IGRT system, a proton beam radiation therapy (PBRT) system, a light ion radiation therapy system, a heavy ion radiation therapy system.

Figure 2:
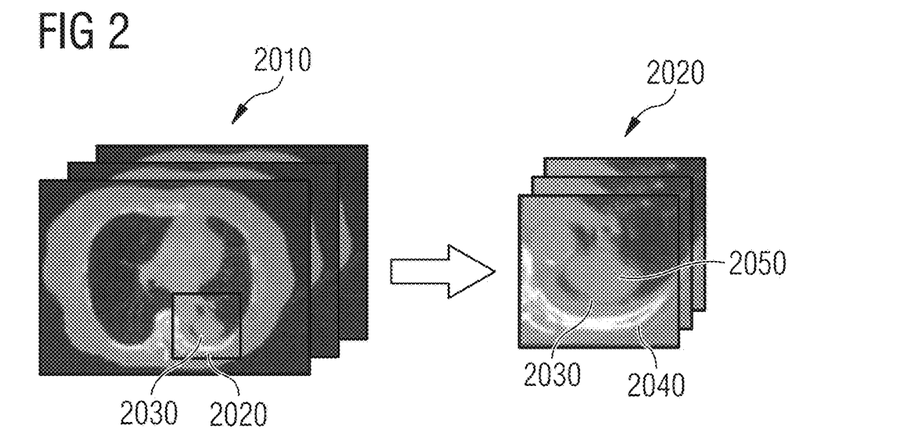
FIG. 2 schematically illustrates a target region of a radiotherapy treatment according to various examples.

FIG. 2 schematically illustrates a target region 2030 including a tumor 2050 and a region of interest (ROI) 2020 including the target region 2030. The ROI 2020 can include or be part of a specific organ, such as a lung, a brain, a liver, a pancreas, a kidney and so on. Images of ROI 2020 may be obtained from imaging data 2010 of a patient acquired by using at least one medicine imaging scanning techniques, such as radiographic imaging including CT (computed tomography) and X-ray, nuclear medicine imaging including positron emission tomography (PET) and single-photon emission computerized tomography (SPECT), MRI (magnetic resonance imaging) scans, ultrasound imaging and etc. (cf. TAB. 2, example II).

Within the ROI 2020, there are healthy/normal tissues/cells 2040 surrounding the target region 2030. During the radiotherapy treatment, both tumor cells and healthy cells within the target region 2030 as well as healthy cells closely surrounding the target region 2030 are irradiated by radiation—emitted by, e.g., the linac 1000 according to FIG. 1. In a period of time after the radiotherapy treatment, the healthy cells within the ROI 2020 may suffer from radiation-induced damages or diseases, e.g., radiation-induced pneumonitis.

A radiation oncologist, when planning a radiotherapy treatment for a patient with cancer, determines a treatment plan including a radiation dose that is large enough to potentially cure or control the disease within the target region 2030, but does not cause serious healthy/normal tissue complications, such as radiation-induced toxicity. Various examples are based on the finding that this task can be challenging, because tumor control and healthy/normal tissue effect responses are typically steep functions of radiation dose; that is, a small change in the dose delivered (±5%) can result in a change in the local response of the tissue (±20%). Moreover, the prescribed curative doses are often, by necessity, very close to the doses tolerated by the healthy/normal tissues. Because of this small "therapeutic window" for optimum treatment, the radiation dose must be planned and delivered with a high degree of accuracy to avoid serious normal tissue complications, such as radiation-induced toxicity.

According to various examples, an individual patient can be assigned a score (cf. TAB. 1)—i.e., the at least one toxicity indicator—indicating his/her level of vulnerability to radiation-induced toxicity, then this information can be used to modify the treatment plan, e.g., to thereby obtain a modified dose map.

Thus, according to the techniques described herein a predictive method is provided that, based on various pre-treatment diagnostic or planning tests such as radiographic imaging scans, nuclear medicine imaging scans, MRI scans, ultrasound imaging scans and other clinical data such as EEG (electroencephalogram), ECG (electrocardiogram), can determine the at least one radiation-induced toxicity indicator as a risk score quantifying the toxicity level the patient could potentially experience after the therapy.

Hereinafter, techniques of machine-learning, particularly deep-learning, for predicting risks of radiation-induced toxicity associated with a radiotherapy treatment of a target region of a patient are described. Supervised learning relying on labeled training data can be used to parameterize a machine-learning algorithm. In supervised learning, a target variable is known as ground truth, and a machine-learning algorithm can learn the pattern between dependent and independent variables.

Figure 3:
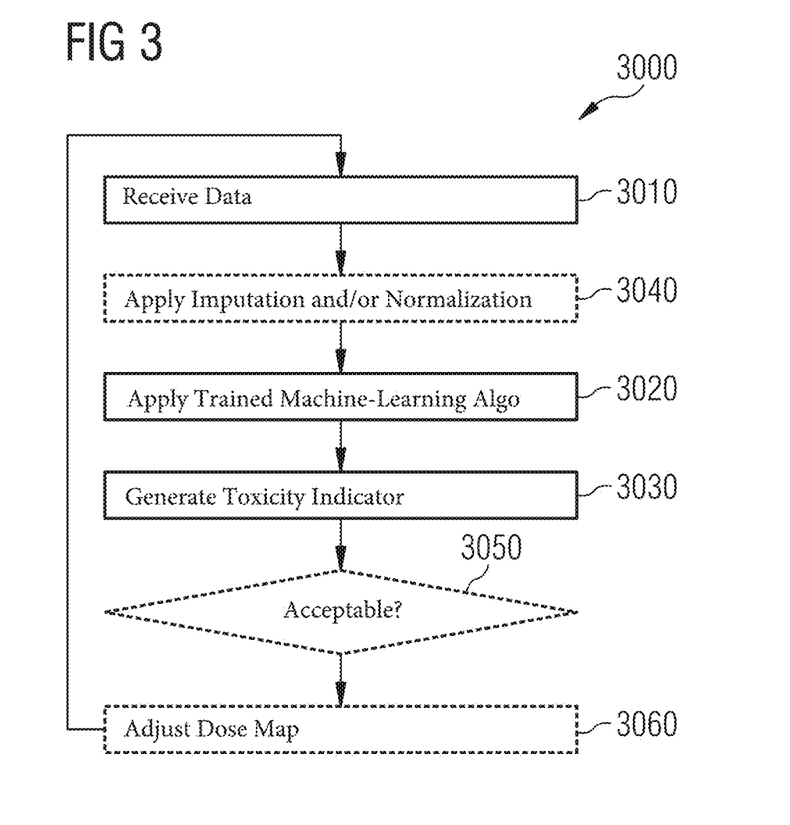
FIG. 3 is a flowchart of a method according to various examples.

First—in connection with FIG. 3—details with respect to the inference of at least one toxicity indicator are described, based on a pre-trained machine-learning algorithm. The training will be later-on explained in connection with FIG. 5.

FIG. 3 is a flowchart of a method 3000 according to various examples. Optional blocks are labeled with dashed lines. For example, the method 3000 according to FIG. 3 may be executed by a computing device (computer) directly or remotely connected to the linac 1000 according to the example of FIG. 1 or another radiation-therapy hardware, e.g., upon loading program code from a memory. It would also be possible that the method 3000 is at least partially executed by a separate compute unit, e.g., at a server backend or using cloud computing. The computing device or the separate compute unit may include at least one circuit—e.g., a central processing unit (CPU) and/or a graphics processing unit (GPU) and/or a tensor processing unit (TPU)—for executing the method 3000.

The method 3000 can predict risks of radiation-induced toxicity based on pre-treatment data capturing underlying and subtle signatures of healthy tissues surrounding a tumor, e.g., lung parenchyma, vulnerability to radiation. Such information may be combined with planning medicine imaging scans as mentioned above and a planned dose map capturing both the tumor characteristics and potential dosimetric level and its distribution over not only the tumor but the surrounding presumably healthy tissues, e.g., lung parenchyma.

In detail, at block 3010, the computing device or the separate compute unit receives data associated with a ROI (e.g., ROI 2020 according to FIG. 2) including the target region 2030. The data may be received from a database or a clinical planning system. The data may be received from a memory.

At block 3010, input data according to TAB. 2 may be used. Specifically, the received data may include a pre-defined dose map of the radiotherapy treatment and pre-radiotherapy-treatment imaging data of the ROI 2020.

For example, pre-radiotherapy-treatment imaging data of the ROI 2020 may be used (cf. TAB. 2, option II). This imaging data may include at least one of X-ray imaging data, CT imaging data, MRI imaging data, PET imaging data, SPECT imaging data, ultrasound imaging data. If the pre-radiotherapy-treatment imaging data includes two and more imaging data of different imaging modalities, registration may be applied to the pre-radiotherapy-treatment imaging data, e.g., registering CT imaging data with MRI imaging data, and/or PET imaging data. Further, the pre-radiotherapy-treatment imaging data may be registered with the predefined dose map.

The received data may further include at least one of a dose level (e.g., 8 Gy) of the radiotherapy treatment, a clinical stage of a tumor located in the target region, comorbidities of the patient, and/or demographics of the patient, as previously explained in connection with TAB. 2.

At block 3020, the computing device or the separate compute unit applies a trained machine-learning algorithm to the received data.

As a general rule, according to the various examples described herein, the trained machine-learning algorithm may be a (deep) neural network, e.g., a convolutional neural network, a recurrent neural network, a generative adversarial network, a residual network and etc. For example, the trained machine-learning algorithm includes an encoder for extracting pertinent features (sometimes also referred to as latent features) of the ROI based on the received data and a classifier for generating the at least one toxicity indicator based on the extracted pertinent features of the ROI.

Further, the trained machine-learning algorithm may be obtained by utilizing supervised learning, semi-supervised learning, or reinforcement learning. Preferably, the trained machine-learning algorithm is trained by using supervised learning. A computer-implemented method of performing a training to obtain the trained machine-learning algorithm will be explained below later in connection with FIG. 5.

At block 3030, at least one toxicity indicator is generated based on the received data via the trained machine-learning algorithm. The at least one toxicity indicator is indicative of the risks of the radiation-induced toxicity and thereby shows a prediction of potential level of radiation-induced toxicity. Details have been explained in connection with TAB. 1.

Optionally, the method 3000 may further include, at block 3040, applying imputation and/or normalization to the received data before applying the trained machine-learning algorithm to the received data.

Imputation is the process of replacing missing data with substituted values. When the received data miss a certain amount of information, such as a pixel value of a pre-radiotherapy-treatment image, imputation may be used to determine the missed pixel value based on pixel values of pixels surrounding the pixel. Imputation may include hot-deck imputation, Cold-deck imputation, mean imputation, Regression imputation, and multiple imputation.

Normalization may include batch normalization, weight normalization, layer normalization, instance normalization, group normalization, batch renormalization, batch-instance normalization, and so on.

Optionally, the method 3000 may further include, at block 3050, assessing whether the at least one generated toxicity indicator indicates acceptable radiation-induced toxicity, i.e., the predefined dose map is acceptable (or optimal), based on the at least one generated toxicity indicator.

Such an assessment may be performed by comparing each of the at least one generated toxicity indicator with a corresponding threshold of respective toxicity indicator. Other predefined rules may be used. Patient-specific rules could be applied.

Optionally, when at least one generated toxicity indicator, i.e., the predefined dose map, is not acceptable (or sub-optimal), the method 3000 may additionally include, at block 3060, adjusting the predefined dose map based on the at least one generated toxicity indicator to generate a further predefined dose map. Then, the method 3000 can be iteratively executed by replacing the predefined dose map with the further predefined dose map until acceptable (or optimal) toxicity indicators, i.e., predefined dose map, are generated.

For example, in the beginning, a predefined dose map M1 is received and processed by the trained machine-learning algorithm together with the other data, such as the pre-radiotherapy-treatment imaging data, and thereby a toxicity indicator T1 is generated by the trained machine-learning algorithm. The toxicity indicator T1 may be assessed by experienced radiation oncologists or by comparing with a threshold of toxicity indicator value, to determine whether the predefined dose map M1 is optimal or not. An automated analysis may be used instead.

If the predefined dose map M1 is determined to be sub-optimal, a further predefined dose map M2 is generated by adjusting the previous predefined dose map M1 based on the previous toxicity indicator T1. Then, this adjusted dose map M2 is used to predict the risks of the radiation-induced toxicity with the respectively defined radiotherapy treatment, and thereby a further toxicity indicator T2 is generated by the trained machine-learning algorithm. The toxicity indicator T2 may be assessed in the same manner as T1.

The above-mentioned actions—generating a further predefined dose map Mn, receiving the further dose map Mn, processing the further dose map Mn together with the same other data by the same trained machine-learning algorithm, generating a further toxicity indicator Tn, and assessing the further toxicity indicator Tn—may be iteratively executed until the optimal (or maybe suboptimal) predefined dose map is determined.

Figure 4:
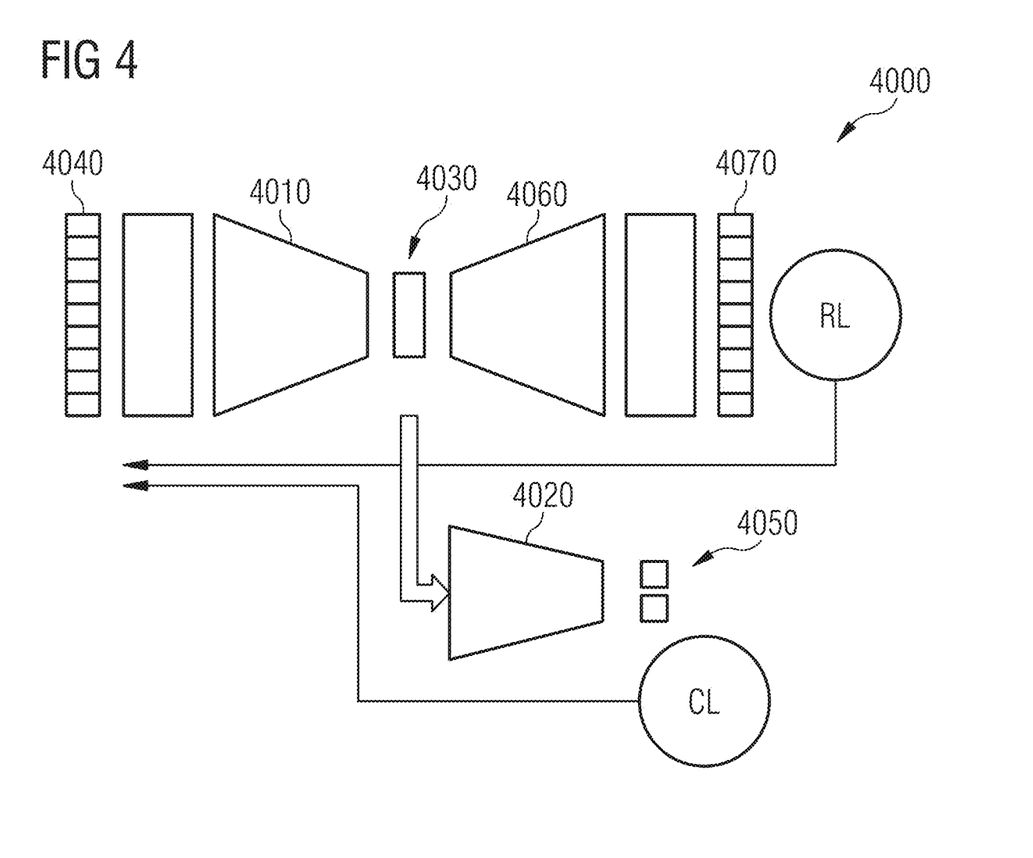
FIG. 4 schematically illustrates an exemplary realization of a machine-learning algorithm according to various examples.

FIG. 4 schematically illustrates an exemplary implementation of a machine-learning algorithm that can be used in the various examples described herein. The machine-learning algorithm is implemented as a neural network 4000. The neural network 4000 includes an encoder 4010 for extracting pertinent features 4030 of input data 4040 (such as data associated with the ROI 2020) and a classifier 4020 for generating at least one toxicity indicator 4050 based on the extracted pertinent features 4030 of the input data 4040.

After performing a training of the neural network 4000— e.g., by using supervised learning, semi-supervised learning, or reinforcement learning—to determine parameters and possibly hyper-parameters of the neural network 4000, the trained neural network 4000 can be utilized to process the data 4040 (cf. TAB. 2) associated with the ROI 2020 to determine at least one toxicity indicator indicative of the risks of the radiation-induced toxicity. Details with respect to the training are described in connection with FIG. 5.

Figure 5:
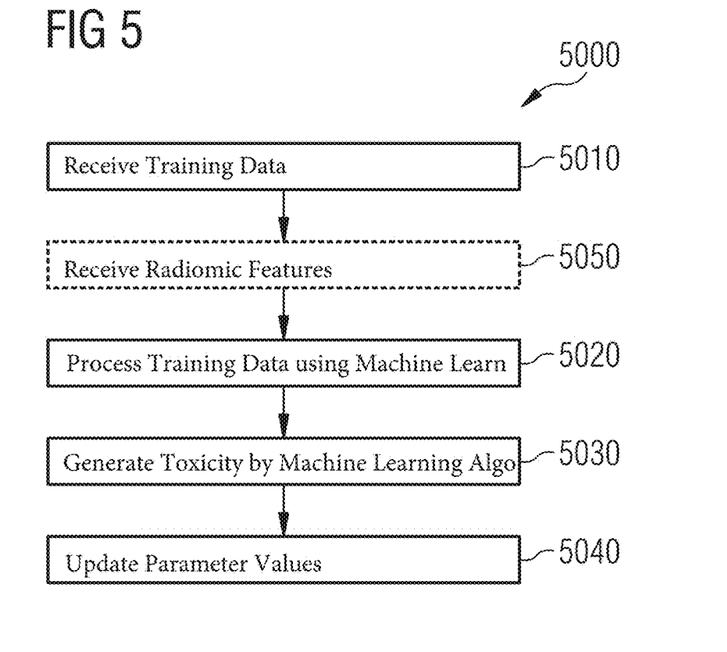
FIG. 5 is a flowchart of a further method according to various examples.

FIG. 5 is a flowchart of a method 5000 for performing a training of a machine-learning algorithm (such as the neural network 4000 as shown in FIG. 4). The trained machine-learning algorithm can then be used for the method 3000 of FIG. 3. The method 5000 may be executed by the same computing device that executes the method 3000, or by a different computing device.

The method 5000 is a computer-implemented method of performing a training of a machine-learning algorithm for predicting risks of radiation-induced toxicity associated with a radiotherapy treatment of a target region (e.g., 2030 according to FIG. 2) of a patient.

In detail, at block 5010, multiple instances of training data associated with a ROI (e.g., ROI 2020 according to FIG. 2) including the target region (e.g., 2030 according to FIG. 2) are received. Also, multiple instances of reference data are received, each one of the multiple instances of the reference data corresponding to a respective instance of the training data. Each one of the multiple instances of the training data includes a dose map of the radiotherapy treatment and pre-radiotherapy-treatment imaging data of the ROI 2020. Each instance of the multiple instances of the reference data includes at least one diagnosed toxicity indicator indicative of diagnosed risks of radiation-induced toxicity—thus serving as a ground truth.

The multiple instances define a training dataset. Typically, a larger training dataset can be helpful to achieve more accurate training.

The multiple instances of training data may include pre-radiotherapy-treatment data associated with various patients suffering from the same type of cancers/tumors, which ensure that the ROI 2020 and the target region 2030 have the same or at least similar anatomical and physiological characteristics and thereby the multiple instances of training data may be regarded as instances based on the same probability distribution. The multiple instances of reference data may include post-radiotherapy-treatment data associated with the same various patients suffering from the same type of cancers/tumors and obtained after undergoing the radiotherapy treatment. The multiple instances of training data and the multiple instances of reference data may have a one-to-one correspondence (or bijection).

Similar to the received data according to method 3000, each one of the multiple instances of the training data may further include at least one of a dose level (e.g., expressed in units of Gray) of the radiotherapy treatment, a clinical-stage of a tumor located in the target region, comorbidities of a further patient, and/or demographics of the further patient. Respective examples have been described in connection with TAB. 2.

The at least one diagnosed toxicity indicator—details have been explained in connection with TAB. 1—may obtained by manually or automatically analyzing the post-radiotherapy-treatment data.

In some examples, it is possible that the at least one diagnosed toxicity indicator corresponding to each instance of the multiple instances of the reference data is generated by a further trained machine-learning algorithm based on diagnosed data obtained at two or more time points after the radiotherapy treatment, and each one of the diagnosed data includes imaging data of the ROI. Here, it would be possible to use techniques disclosed in "Machine Learning Automatically Detects COVID-19 using Chest CTs in a Large Multicenter Cohort" arXiv:2006.04998. In particular, it would be possible to consider changes in the diagnosed data for the different time points. Such changes can be indicative of toxicity, e.g., due to changes in the tissue. For instance, it would be possible to compare the imaging data of the ROI obtained at the two or more time points, e.g., in a pixel wise manner upon performing a registration. Then, changes in the contest can be indicative of radiation-induced toxicity.

Accordingly, the method 5000 may further include performing a registration of the imaging data of the ROI obtained at the two or more time points with each other or with the pre-radiotherapy-treatment imaging data.

At block 5020, the multiple instances of the training data are processed using the machine-learning algorithm. Optionally, the method 5000 may further include applying imputation and/or normalization to each one of the multiple instances of the training data before processing the multiple instances of the training data by the machine-learning algorithm.

At block 5030, at least one respective estimated toxicity indicator indicative of estimated risks of radiation-induced toxicity is generated by the machine-learning algorithm, for each one of the multiple instances of the training data. The at least one estimated toxicity indicator may be regarded as an estimate of the at least one diagnosed toxicity indicator—according to the current training state of the machine-learning algorithm.

At block 5040, the computing device performs the training of the machine-learning algorithm by updating parameter values of the machine-learning algorithm based on a comparison between the diagnosed toxicity indicators and corresponding estimated toxicity indicators. The larger a deviation, the poorer the respective training state of the machine-learning algorithm. A loss function can be defined. Optimization techniques can be employed to adjust the parameters, e.g., backpropagation, etc.

Referring to FIG. 4, the neural network 4000 can include a decoder 4060. Using the decoder 4060, the training can be facilitated. Based on an output 4070 of the decoder 4060, it is possible to adjust parameters of both the encoder 4010 and the classifier 4020 when performing the training. Thereby, a better performance of the classifier 4020 can be achieved, i.e., the at least one toxicity indicator 4050 can be accurately determined.

The decoder 4060 may generate reconstructed input data as the output 4070. The reconstructed input data of the output 4070 corresponds to the reference data. Alternatively, the decoder 4060 may generate multiple instances of estimated radiomic features as the output 4070 of the ROI based on the pertinent features 4030 of the training data. The estimated radiomic features of the output 4070 may include intensity, geometry, texture, and wavelet features of the ROI.

As described above, the encoder 4010 and the classifier 4020 may be trained jointly based on a classification loss Cl, i.e., by updating parameter values of both the encoder 4010 and the classifier 4020 based on a comparison between the diagnosed toxicity indicators and corresponding estimated toxicity indicators.

Alternatively, or additionally, the encoder 4010, the classifier 4020 and the decoder 4060 may be trained jointly based on a sum or a weighted sum of the classification loss Cl and a reconstruction loss Rl, i.e., Cl+Rl or w1*Cl+w2*Rl, wherein w1 and w2 are manually selected or hyperparameters adjusted during the training. Once the training is done, only the encoder 4010 and the classifier 4020 will be used to predict risks of radiation-induced toxicity associated with a radiotherapy treatment of a target region of a patient, for example by executing the method 3000.

Thus, the method 5000 may optionally further includes generating reconstructed data based on the training data using the decoder 4060 of the machine-learning algorithm. Then, the updating of the parameter values of the machine-learning algorithm is further based on a comparison between each one of the multiple instances of the training data and corresponding reconstructed data.

Alternatively, the method 5000 may optionally include receiving multiple instances of diagnosed radiomic features of the ROI in block 5050, for example together with various data received at block 5010, and generates multiple instances of estimated radiomic features of the ROI via the decoder 4060. The diagnosed radiomic features may be extracted from gross tumour volumes encompassing regions of interest. The diagnosed radiomic features may include intensity, geometry, texture, and wavelet features of the ROI. The intensity features quantified the first-order statistical distribution of the voxel intensities within the gross tumor volumes. The geometry features quantified shape characteristics of the tumor. The texture features described spatial distribution of the voxel intensities, thereby quantifying the intratumoral heterogeneity. The intensity and texture features may be also computed after applying wavelet transformations to the original image. The diagnosed radiomic features may be handcrafted by experts or computed based on predefined mathematical formulas. The machine-learning algorithm further includes the decoder 4060 for generating the estimated radiomic features of the ROI based on the extracted pertinent features of the ROI. The updating of the parameter values of the machine-learning algorithm is further based on a comparison between each one of the multiple instances of the diagnosed radiomic features of the ROI and corresponding estimated radiomic features of the ROI.

Figure 6:
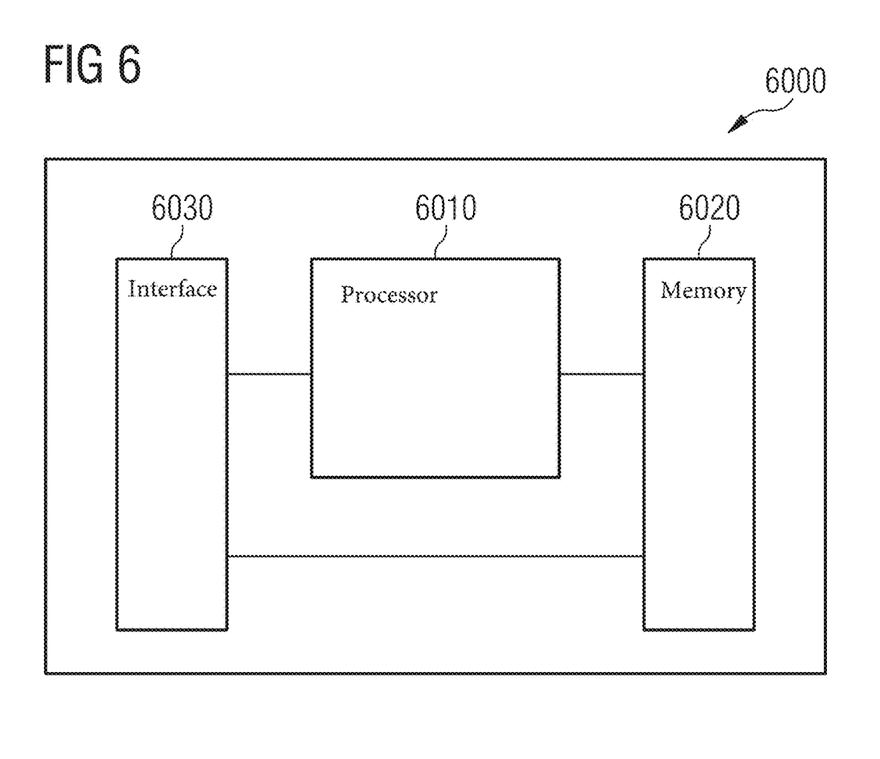
FIG. 6 schematically illustrates a device according to various examples.

FIG. 6 schematically illustrates a device 6000 according to various examples. The device 6000 may be the computing device mentioned above. The device 6000 includes a processing unit 6010, a memory unit 6020 and an input/output interface 6030. The processing unit 6010 is configured to execute a program stored in the memory unit 6020 to perform the method 3000 and/or the method 5000. The input/output interface 6030 may communicate with actuators associated with the dosimetry system 1010 and/or the collimation system 1011 to adjust radiation doses of a radiotherapy treatment.

Summarizing, above, techniques have been described that facilitate predicting—prior to a radiotherapy treatment—a patient's vulnerability to radiation-induced toxicity and potential manifestation of radiation-induced toxicity after the radiotherapy by utilizing artificial intelligence (AI) techniques to extract pertinent features (i.e., disease fingerprint) from patient imaging data acquired at planning phase. This task-specific fingerprint is computed directly from imaging data of patients with similar/the same disease and treatment. Therefore, it only includes information closely related to the radiation-induced toxicity. These fingerprints are different from classical radiomics features as they are not generic measurements and are trained to be most discriminative for specific conditions or events. The algorithm also learns the causality between applied dose and tissue changes in the ROI and thereby predicts the possible extension of radio-toxicity.

In particular, patients to be treated with radiotherapy can be stratified based on a likelihood of toxicity as indicated by at least one toxicity indicator and high-risk patients could be flagged to be managed differently. Furthermore, a dose level and/or a dose map as input could be adjusted to compute a new toxicity score to a certain threshold for example. I.e., offering a dose prescription solution that uses data from a large cohort of outcome matched patients with known planning dose and toxicity profile to help an oncologist find an optimal dose with respect both outcome and toxicity profile for a specific patient.

Thus, radiotherapy treatments can be precisely and reliably individualized based on anatomical and physiological characteristics of individual patients and thereby can give clinicians a chance to select a radiotherapy treatment that is most likely to be adapted to an individual patient to maximize the likelihood of treatment response while minimizing the risk of adverse effects, such as radiation-induced toxicity.

The invention claimed is:

1. A computer-implemented method for predicting risks of radiation-induced toxicity associated with a radiotherapy treatment of a target region of a patient, the method comprising:

receiving data associated with a region of interest comprising the target region, wherein the received data comprises a predefined dose map of the radiotherapy treatment and pre-radiotherapy-treatment imaging data of the region of interest;

applying a trained machine-learning algorithm to the received data, the trained machine-learning algorithm having been trained by: (1) processing multiple instances of training data by the machine-learning algorithm, the multiple instances of training data associated with the region of interest comprising the target region and multiple instances of reference data, each one of the multiple instances of the reference data corresponding to a respective instance of the training data, wherein each one of the multiple instances of the training data comprises the dose map of the radiotherapy treatment and the pre-radiotherapy-treatment imaging data of the region of interest, wherein each instance of the multiple instances of the reference data comprises at least one diagnosed toxicity indicator indicative of diagnosed risks of radiation-induced toxicity, and (2) updating parameter values of the machine-learning algorithm based on a comparison between diagnosed toxicity indicators and corresponding estimated toxicity indicators by the machine-learning algorithm; and generating, by the trained machine-learning algorithm, at least one toxicity indicator based on the received data, wherein the at least one toxicity indicator is indicative of the risks of the radiation-induced toxicity.

2. The method of claim 1, wherein the received data further comprises at least one of the following:
a dose level of the radiotherapy treatment,
a clinical stage of a tumor located in the target region,
comorbidities of the patient, and/or
demographics of the patient.

3. The method of claim 1, further comprising,
applying imputation to the received data; and/or
applying normalization to the received data.

4. The method of claim 1,
wherein the at least one toxicity indicator comprises at least one of an aggregated risk score, a dose sensitivity for characterizing effects of doses indicated by the predefined dose map on the radiation-induced toxicity, or a toxicity area map of the region of interest.

5. The method of claim 1, further comprising:
adjusting the predefined dose map based on the at least one toxicity indicator.

6. The method of claim 1,
wherein the trained machine-learning algorithm comprises an encoder for extracting pertinent features of the region of interest based on the received data and a classifier for generating the at least one toxicity indicator based on the extracted pertinent features of the region of interest.

7. The method of claim 1, wherein the received data further comprises at least one of the following:
a dose level of the radiotherapy treatment,
a clinical stage of a tumor located in the target region,
comorbidities of the patient, and/or
demographics of the patient;
wherein the at least one toxicity indicator comprises at least one of an aggregated risk score, a dose sensitivity for characterizing effects of doses indicated by the predefined dose map on the radiation-induced toxicity, or a toxicity area map of the region of interest; and wherein the trained machine-learning algorithm comprises an encoder for extracting pertinent features of the region of interest based on the received data and a classifier for generating the at least one toxicity indicator based on the extracted pertinent features of the region of interest.

8. A computer-implemented method of performing a training of a machine-learning algorithm for predicting risks of radiation-induced toxicity associated with a radiotherapy treatment of a target region of a patient, the method comprising:
receiving multiple instances of training data associated with a region of interest comprising the target region and multiple instances of reference data, each one of the multiple instances of the reference data corresponding to a respective instance of the training data, wherein each one of the multiple instances of the training data comprises a dose map of the radiotherapy treatment and pre-radiotherapy-treatment imaging data of the region of interest, wherein each instance of the multiple instances of the reference data comprises at least one diagnosed toxicity indicator indicative of diagnosed risks of radiation-induced toxicity;
processing the multiple instances of the training data by the machine-learning algorithm;
generating, by the machine-learning algorithm and for each one of the multiple instances of the training data, at least one respective estimated toxicity indicator indicative of estimated risks of radiation-induced toxicity; and
performing the training of the machine-learning algorithm by updating parameter values of the machine-learning algorithm based on a comparison between the diagnosed toxicity indicators and corresponding estimated toxicity indicators.

9. The method of claim 8, wherein the training data further comprises at least one of the following:
a dose level of the radiotherapy treatment,
a clinical stage of a tumor located in the target region,
comorbidities of a further patient, and/or
demographics of the further patient.

10. The method of claim 8, further comprising:
applying imputation to each one of the multiple instances of the training data; and/or
applying normalization to each one of the multiple instances of the training data.

11. The method of claim 8,
wherein the at least one diagnosed toxicity indicator and the at least one estimated toxicity indicator comprise at least one of a diagnosed aggregated risk score, a dose sensitivity for characterizing effects of doses indicated by the dose map on the radiation-induced toxicity, or a diagnosed toxicity area map of the region of interest.

12. The method of claim 8,
wherein the machine-learning algorithm comprises an encoder for extracting pertinent features of the region of interest based on the received data and a classifier for generating the at least one estimated toxicity indicator based on the extracted pertinent features of the region of interest.

13. The method of claim 12, further comprising:
generating reconstructed data based on the training data using a decoder of the machine-learning algorithm;
wherein the updating of the parameter values of the machine-learning algorithm is further based on a comparison between each one of the multiple instances of the training data and corresponding reconstructed data.

14. The method of claim 12, further comprising:

receiving multiple instances of diagnosed radiomic features of the region of interest;

generating multiple instances of estimated radiomic features of the region of interest;

wherein the machine-learning algorithm further comprises a decoder for generating the estimated radiomic features of the region of interest based on the extracted pertinent features of the region of interest;

wherein the updating of the parameter values of the machine-learning algorithm is further based on a comparison between each one of the multiple instances of the diagnosed radiomic features of the region of interest and corresponding estimated radiomic features of the region of interest.

15. The method of claim 8, wherein the at least one diagnosed toxicity indicator corresponding to each instance of the multiple instances of the reference data is generated by a further trained machine-learning algorithm based on diagnosed data obtained at two or more time points after the radiotherapy treatment, and each one of the diagnosed data comprises imaging data of the region of interest.

16. The method of claim 15, further comprises:

performing a registration of the imaging data of the region of interest obtained at the two or more time points.

17. The method of claim 8, wherein the training data further comprises at least one of the following: a dose level of the radiotherapy treatment, a clinical stage of a tumor located in the target region, comorbidities of a further patient, and/or demographics of the further patient;

wherein the at least one diagnosed toxicity indicator and the at least one estimated toxicity indicator comprise at least one of a diagnosed aggregated risk score, a dose sensitivity for characterizing effects of doses indicated by the dose map on the radiation-induced toxicity, or a diagnosed toxicity area map of the region of interest;

wherein the machine-learning algorithm comprises an encoder for extracting pertinent features of the region of interest based on the received data and a classifier for generating the at least one estimated toxicity indicator based on the extracted pertinent features of the region of interest;

wherein the at least one diagnosed toxicity indicator corresponding to each instance of the multiple instances of the reference data is generated by a further trained machine-learning algorithm based on diagnosed data obtained at two or more time points after the radiotherapy treatment, and each one of the diagnosed data comprises imaging data of the region of interest.

\* \* \* \* \*